United States Patent

Dotta et al.

[11] Patent Number: 6,062,285
[45] Date of Patent: May 16, 2000

[54] MACHINE FOR MANUFACTURING ADHESIVE DRESSINGS HAVING THE ABSORBING COMPRESS COMPLETELY SURROUNDED BY THE ADHESIVE SUPPORT

[75] Inventors: Angelo Dotta, Bologna; Giorgio Dotta, Lippo di Calderara di Reno, both of Italy

[73] Assignee: Plastod SpA, Bologna, Italy

[21] Appl. No.: 08/750,696

[22] PCT Filed: Jun. 26, 1995

[86] PCT No.: PCT/EP95/02474

§ 371 Date: Dec. 16, 1996

§ 102(e) Date: Dec. 16, 1996

[87] PCT Pub. No.: WO96/00544

PCT Pub. Date: Jan. 11, 1996

[30] Foreign Application Priority Data

Jun. 29, 1994 [IT] Italy .................................. TO94A0532

[51] Int. Cl.[7] .............................. B32B 31/00; A61F 13/02
[52] U.S. Cl. .......................... 156/512; 156/358; 156/520; 156/522; 156/552; 156/265; 156/270; 156/301; 156/302; 156/308.4; 83/346; 53/520; 53/435; 604/304
[58] Field of Search ...................................... 156/520, 519, 156/517, 522, 516, 358, 357, 353, 362, 512, 552, 265, 270, 301, 302, 308.4; 604/358, 379, 304, 307; 83/346, 260, 343; 53/520, 435; 226/153

[56] References Cited

U.S. PATENT DOCUMENTS

| | | |
|---|---|---|
| 2,711,739 | 6/1955 | Fishbein . |
| 2,946,281 | 7/1960 | Sohn ........................................ 101/227 |
| 3,325,335 | 6/1967 | Martensson ............................... 156/498 |
| 4,214,936 | 7/1980 | Del Bianco .............................. 156/302 |
| 4,235,337 | 11/1980 | Dotta ....................................... 206/441 |
| 4,779,781 | 10/1988 | Billberg et al. ............................ 226/2 |
| 4,919,027 | 4/1990 | Littleton .................................... 83/346 |

FOREIGN PATENT DOCUMENTS

| | | |
|---|---|---|
| 0573708 A1 | 12/1993 | European Pat. Off. . |
| 2 494 166 | 5/1992 | France . |

OTHER PUBLICATIONS

Paatent Abstract of Japan vol. 8 No. 108 (M–297), May 19, 1984 (see abstract) for JP5901915.
English Abstract for DE 3145912 A Jun. 9, 1982 Dialog (R) 351–World Patent Index.

*Primary Examiner*—Curtis Mayes
*Assistant Examiner*—Linda L Gray
*Attorney, Agent, or Firm*—Helfgott & Karas, PC.

[57] ABSTRACT

A machine for manufacturing adhesive dressings having an adhesive support, absorbing material compresses laying on the support and a protective layer, includes a cutting element for cutting compresses to a desired size and placing them at the desired intervals onto the adhesive layer. The cutting element includes a first cylindrical counter roll that has a smooth surface and a second roll acting on the first roll. The second roll has projecting sectors, alternated with recessed sectors, provided with at least a transversal cutting knife for cutting the absorbing tape by compressing the same against the counter roll. The tape is drawn during the synchronous rotation of the rolls by the projecting sectors cooperating with the surface of the counter roll. Each knife is positioned close to the transition region between a projecting sector and a subsequent recessed sector to provide a trailing projection portion for each projecting sector so that the absorbing material compresses are held between the first and second rolls by the trailing portion after being cut and before being supplied to the adhesive support.

5 Claims, 2 Drawing Sheets

MACHINE FOR MANUFACTURING ADHESIVE DRESSINGS HAVING THE ABSORBING COMPRESS COMPLETELY SURROUNDED BY THE ADHESIVE SUPPORT

BACKGROUND OF THE INVENTION

1. Field of the Invention

The present invention relates to a machine for manufacturing adhesive dressings.

More particularly the invention relates to a machine for manufacturing small sized "strips" type and large sized "island dressing" type surgical adhesive dressings having a length comprised between 8 and 35 cm and a width comprised between 8 and 10 cm.

2. Description of the Prior Art

Conventional machines used for manufacturing adhesive dressings of the aforementioned type have alternate or rotary movement.

The adhesive support is unwound from rolls, separated from its protective film and perforated if necessary.

Absorbing compresses, obtained by transversely cutting a tape of absorbing material, are then applied onto said adhesive support at the required intervals.

Then a protective material generally made of silicone paper is applied which covers both the adhesive support and the absorbing compresses.

The so obtained product is then guided through a cutting zone wherein cutting and trimming are carried out by one or more cutting knives to obtain finished dressings of various lengths.

After the aforementioned operations the dressings can be wrapped or enveloped in wrappers or envelopes generally obtained by coupling two tapes of cold or hot weldable material unwound from rolls.

The most complex operations which are to be performed by the machine during the above disclosed manufacturing process are cutting the absorbing material to the desired size and placing the absorbing compresses at the desired intervals.

In the presently known state of the art these operations need to be carried out by several cooperating means.

More particularly, known machines include drawing and feeding means, e.g. pairs of rolls suitably synchronized, cutting means, e.g. alternative or rotating cutting knives, spacing means, e.g a further pair of rolls or suckers or suction means.

SUMMARY OF THE INVENTION

An object of the present invention is to provide a machine for manufacturing adhesive dressings of the above referred type wherein all the described operations for preparing and placing the absorbing material compresses are carried out by a single device.

Another object of the present invention is to provide the above machine in a form which can be easily manufactured and which is simple and reliable to operate.

A further object of the present invention is to provide the above machine in a form which allows a quick replacement of the parts thereof when a different format for the product is required, as is not infrequently the case.

These and other objects are achieved by the machine of the present invention according to claim 1.

BRIEF DESCRIPTION OF THE DRAWINGS

A detailed description of a preferred, though non-limiting, embodiment of the machine according to the invention is now presented with reference to the following figures.

DETAILED DESCRIPTION

Figure 1:
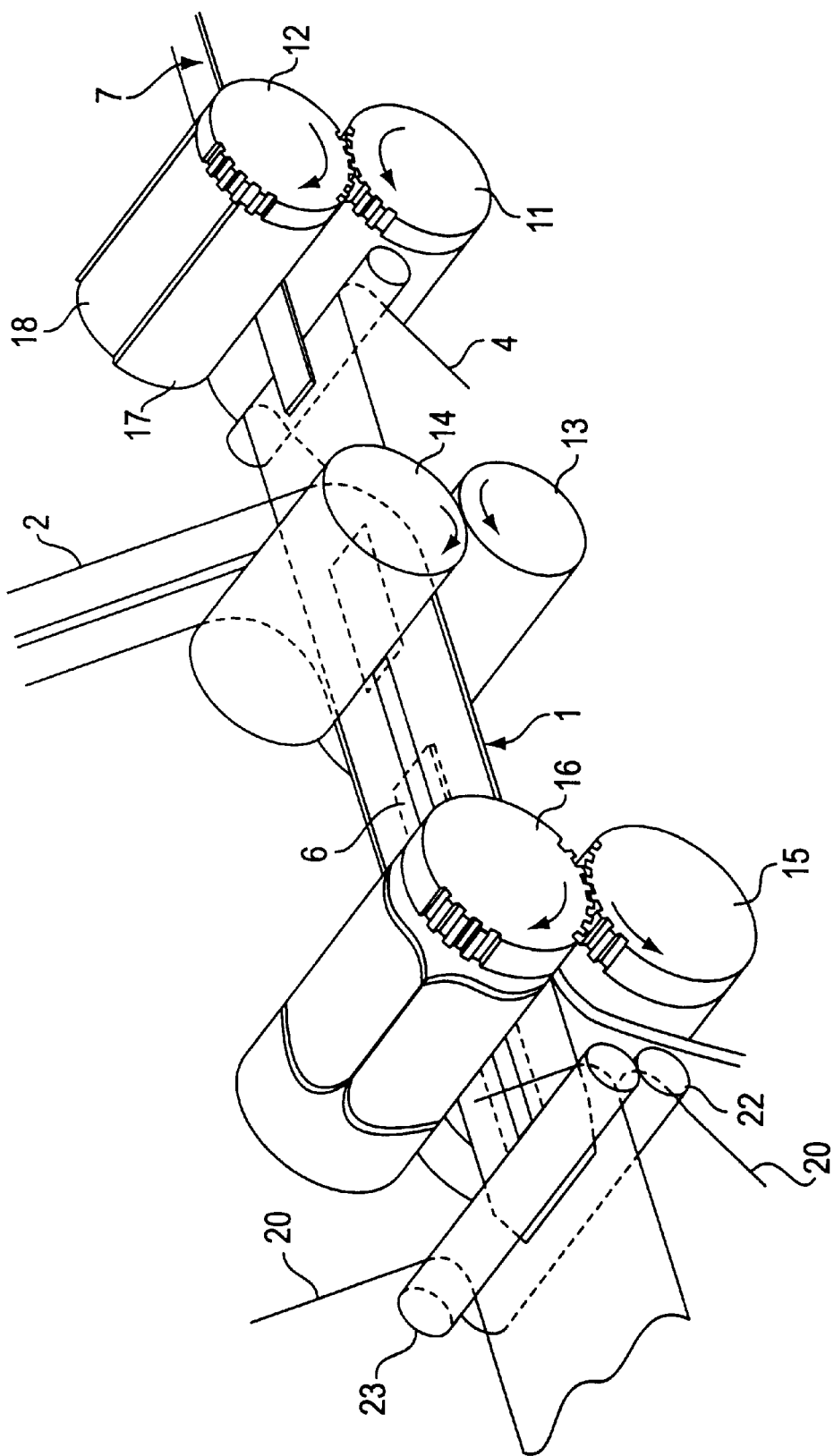
in FIG. 1 the essential parts of the machine according to the invention are illustrated in a schematic general view.

Referring to the attached figures, the adhesive dressing 1 include a protective layer 2 unwound from a roll 3 of a protective material tape, an adhesive support 4, which is separated from its protective film 9 after being unwound from a roll 5, the protective film 9 being rewound on a roll 10 to be recovered, and an absorbing compress 6 obtained by cutting off a tape 7 of absorbing material unwound from a roll 8.

The absorbing dressing 1 manufacturing machine comprises a first pair of rolls 11 and 12 for drawing and cutting the absorbing material tape 7 therebetween, thereby obtaining absorbing compresses 6.

The machine further includes a second pair of rolls 13 and 14 for drawing the adhesive support 4 and the protective layer 2 once the compresses 6 are on the adhesive support 4.

Said pair of rolls 13 and 14 has the further scope of compressing together the adhesive support 4 and the protective layer 2 with the absorbing material compress 6 therebetween for the mutual adhesion thereof.

Through a third pair of rolls 15 and 16 the dressing 1 is cut in portions of the required length.

The coupling of each pair of rolls 11 and 12, 13 and 14, 15 and 16 is obtained by means of gears provided on the peripheral end thereof and ensuring the synchronous reverse rotating movement of the one roll of each pair with respect to the other roll.

Figure 2:
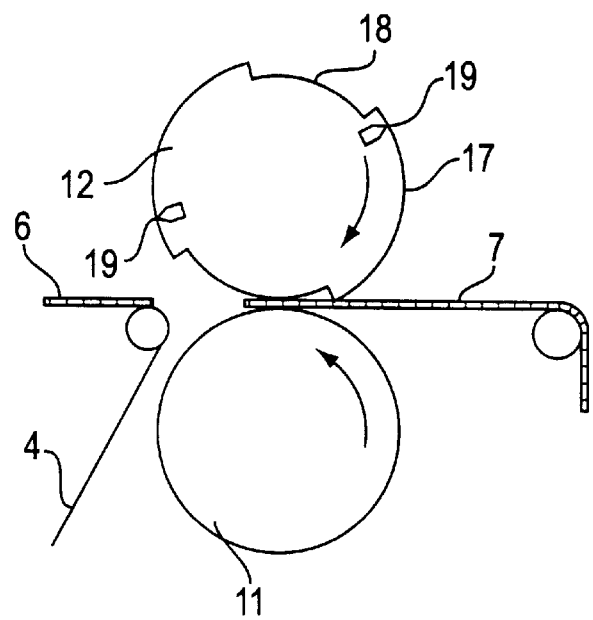
FIG. 2 is a schematic lateral view of absorbing tape cutting rolls.

As better shown in FIG. 2, the pair of rolls 11 and 12 comprises a smooth surface roll 11 having the function of counter roll and a roll 12 having projecting sectors 17 regularly circumferentially alternated with recessed sectors 18.

When the rolls 11 and 12 rotate, the projecting sectors 17 press the absorbing tape 7 against the counter roll 11, thereby drawing the tape therebetween, whereas the recessed sectors 18 maintain the tape 7 substantially not-drawn, being not compressed against the counter roll 11.

Transversal cutting knives 19 which cut the absorbing material by further compressing it against the counter roll 11 are provided in a roll 12 portion corresponding to the projecting sectors 17.

Specifically, the cutting knives 19 are positioned close to the transition region between a projecting sector 17 and the subsequent recessed sector 18 so as to provide, between the recessed sector 18 and the cutting knives 19 according to the roll 12 direction of rotation, a projecting portion of the projecting sector 17 sufficient to hold correctly in position the cut tape 7 between the rolls 11 and 12 before the cut tape 7 is compressed by the subsequent projecting sector 17.

The projecting sectors 17 of the roll 12 are made of semirigid slightly deformable material which allows a slight deformation of the projection during compression of the absorbing material tape 7 against the roll 11.

With the above construction during the synchronized rotation of the three pairs of rolls the feeding of the material is constant only between the pairs of rolls 13, 14 and 15, 16, whereas it becomes intermittent between the pair of rolls 11, 12.

The effect obtained by the roll 12 comprising the projecting sectors 17 and the recessed sectors 18 is that the absorbing tape 7 is transformed into a series of compresses of absorbing material which are regularly spaced and have the same size. The final cutting of the dressing 1 is obtained through a pair of rolls 15, 16 wherein a punched roll 16 compresses and cuts the dressing 1 by pressing it against the counter roll 15.

After being cut, the dressing 1 may pass through a packaging zone wherein the dressing 1 is inserted between two tapes 20 of weldable material unwound from rolls 21 and guided by two idle rolls 22, 23. The distance between the rolls 22 and 23 and the pair of rolls 15 and 16 is set so that during cutting, the forward end of the dressing 1 lies slightly after the pair of rolls 22 and 23 so as to provide for a package of weldable material slightly longer than each dressing to be packaged.

Figure 3:
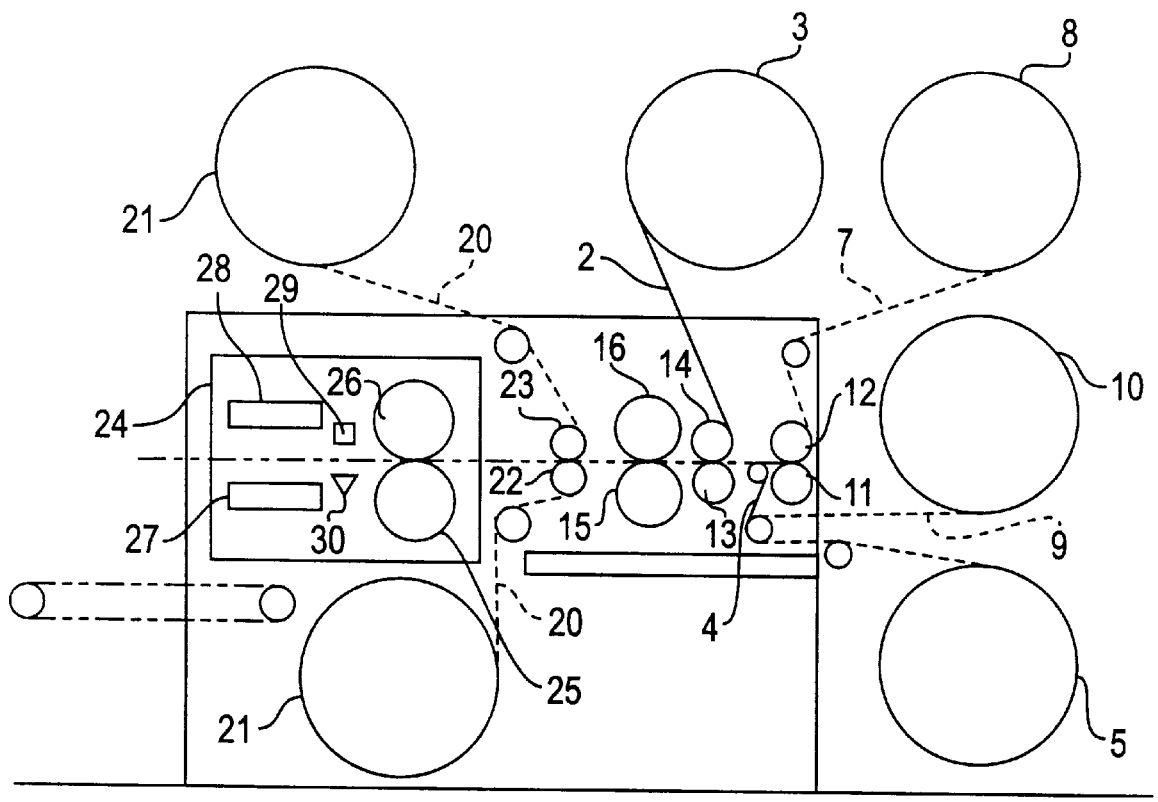
in FIG. 3 the components of a machine for larger dressings comprising a wrapping unit according to the invention are illustrated in a schematic general view.

FIG. 3 shows an example of a machine according to the invention, particularly designed for large sized "island dressing" type dressing wherein a packaging unit referred to as 24 is further provided.

The packaging unit 24 comprises a pair of rolls 25, 26 where the weldable material tapes 20 are drawn and laterally joined together so as to enclose the dressing 1 therebetween.

The joining and transversal cutting of the so packaged dressing are carried out by rotating members 27, 28 which compress and weld the package end portions and further provide for a transversal tear-off line allowing the separation of the packages containing the dressings.

Said rotating members 27, 28 are operated intermittently and pivoted with a peripheral velocity corresponding to the velocity of the rolls 25 and 26.

Control signals produced by a photoelectric sensor 29 energized by means of a light source 30 provide for the synchronized welding and cutting operations by the members 27, 28 in respect of the feeding of the dressing 1.

A more detailed description of the means which carry out the synchronized rotation of the rolls and rotating elements is not deemed necessary as these means are part of the common general knowledge of any man skilled in the art and common to the machines of the state of the art.

What is claimed is:

1. A machine for manufacturing adhesive dressings having an adhesive support, absorbing material compresses laying on said supports and a protective layer, said machine including means for cutting to a predetermined size and placing at predetermined intervals onto the adhesive support the absorbing material compresses obtained from a tape of absorbing material, comprising:

a first cylindrical counter roll having a smooth surface;

a second roll coupled to said first roll by means of gears provided on the peripheral end thereof ensuring a synchronous reverse rotating movement of the second roll with respect to the first roll, said second roll acting on said first roll and having on its surface projecting sectors, regularly circumferentially alternated with recessed sectors, said second roll being further provided with at least one transversal cutting knife for cutting the absorbing tape by compressing the absorbing tape against the first roll;

wherein the absorbing tape is drawn during a synchronous rotation of the rolls only by means of the projecting sectors cooperating with the surface of the first roll, thus enabling the absorbing tape to be intermittently drawn by the rolls so as to supply the absorbent compresses at predetermined intervals onto the adhesive support, said adhesive support being positioned immediately downstream of the cutting means;

wherein the peripheral velocity of said first and second rolls is equal to the adhesive support feeding velocity, thus enabling the interval between the absorbing compresses to be determined only by the length of the recessed sectors of said second roll;

each of said projecting sectors is provided with said knife positioned close to the transition region between a projecting sector and a subsequent recessed sector to provide a trailing projecting portion for each of said projecting sectors, the absorbing material compresses being held between said first and second rolls by the trailing portion after being cut and before being supplied to the adhesive support;

said projecting sectors of the second roll being made of semi-rigid slightly deformable material which allows a slight deformation of the projecting sector during compression of the absorbing material tape against the first roll.

2. The machine according to claim 1, wherein said transversal at least one cutting knife is provided in each projecting sector of the second roll in a position preceding of at least 1 cm the next recessed sector in a direction opposite to the second roll rotation.

3. The machine according to claim 1, further comprising a pair of idle rolls and whereon two converging tapes of weldable material for forming a dressing package are fed between a nip formed by the pair of idle rolls, said pair of idle rolls being provided after a cutting zone for cutting the adhesive dressing.

4. The machine according to claim 3, further comprising means for transversal welding of the dressing package, said welding means being intermittently controlled by signals produced by at least a photoelectric sensor energized by means of a light source when the dressing package is fed therebetween, said photoelectric sensor recognizing a the presence of the dressing package because of the different intensity in the light transmitted by the source.

5. The machine according to claim 4, wherein said means for transversely welding the dressing package includes a pair of rotating members intermittently operated according to the dressing package length.

* * * * *